(12) United States Patent
Merritt et al.

(10) Patent No.: US 6,671,552 B2
(45) Date of Patent: Dec. 30, 2003

(54) SYSTEM AND METHOD FOR DETERMINING REMAINING BATTERY LIFE FOR AN IMPLANTABLE MEDICAL DEVICE

(75) Inventors: Donald R. Merritt, Brooklyn Center, MN (US); Mukul Jain, Maple Grove, MN (US); James W. Busacker, St. Anthony, MN (US); Kathleen U. Crandall, Champlin, MN (US); Karen J. Kleckner, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 206 days.

(21) Appl. No.: 09/970,374

(22) Filed: Oct. 2, 2001

(65) Prior Publication Data

US 2003/0065366 A1 Apr. 3, 2003

(51) Int. Cl.[7] .......................... A61N 1/378; A61N 1/37
(52) U.S. Cl. ................................................. 607/29
(58) Field of Search ............................ 607/4, 5, 9, 27, 607/29

(56) References Cited

U.S. PATENT DOCUMENTS

| | | | |
|---|---|---|---|
| 4,313,079 A | 1/1982 | Lee | 320/48 |
| 4,390,020 A | 6/1983 | Herpers | 607/29 |
| 5,114,810 A | 5/1992 | Frysz et al. | 429/194 |
| 5,180,642 A | 1/1993 | Weiss et al. | 429/90 |
| 5,193,538 A | 3/1993 | Ekwall | 607/29 |
| 5,221,453 A | 6/1993 | Crespi | 204/291 |
| 5,306,581 A | 4/1994 | Taylor et al. | 429/181 |
| 5,331,966 A | 7/1994 | Bennett et al. | 607/28 |
| 5,370,668 A | 12/1994 | Shelton et al. | 607/29 |
| 5,391,193 A | 2/1995 | Thompson | 607/29 |
| 5,439,760 A | 8/1995 | Howard et al. | 429/94 |
| 5,564,434 A | 10/1996 | Halperin et al. | 600/488 |
| 5,620,474 A | 4/1997 | Koopman | 607/29 |
| 5,624,767 A | 4/1997 | Muffoletto et al. | 429/7 |
| 5,626,620 A | 5/1997 | Kieval et al. | 607/9 |
| 5,639,577 A | 6/1997 | Takeuchi et al. | 429/219 |
| 5,667,916 A | 9/1997 | Ebel et al. | 429/218 |
| 5,800,472 A | * 9/1998 | Mann | 607/29 |
| 5,843,139 A | 12/1998 | Goedeke et al. | 607/32 |
| 5,895,733 A | 4/1999 | Crespi et al. | 429/219 |
| 5,931,857 A | 8/1999 | Prieve et al. | 607/14 |
| 6,016,448 A | 1/2000 | Busacker et al. | 607/29 |
| 6,108,579 A | * 8/2000 | Snell et al. | 607/29 |
| 6,157,531 A | 12/2000 | Breyen et al. | 361/519 |
| 6,167,309 A | * 12/2000 | Lyden | 607/29 |
| 6,584,355 B2 | * 6/2003 | Stessman | 607/29 |

FOREIGN PATENT DOCUMENTS

WO    WO 98/02209    1/1998    A61N/1/375

* cited by examiner

Primary Examiner—Carl Layno
(74) Attorney, Agent, or Firm—Girma Wolde-Michael; Daniel G. Chapik

(57) ABSTRACT

A system and method for determining a remaining life estimate of the remaining battery life of a battery of an implantable medical device (IMD). The IMD battery preferably exhibits a highly reproducible monotonically decreasing discharge curve. The estimated remaining life estimates are derived by periodically measuring battery voltage, and estimating the estimated past current drain of the IMD comprising an average of the sum of the quiescent current drain and therapy delivery current drain, and determining the estimated remaining longevity from the measured voltage and the estimated past current drain.

31 Claims, 7 Drawing Sheets

FIG. 6

| I | (I_low) 10 μA | | | 20 μA | | | 40 μA | | | 80 μA | | | (I_high) 160 μA | | |
|---|---|---|---|---|---|---|---|---|---|---|---|---|---|---|---|
| Vb (V) | Avg mo | Max mo | Min mo | Avg mo | Max mo | Min mo | Avg mo | Max mo | Min mo | Avg mo | Max mo | Min mo | Avg mo | Max mo | Min mo |
| 3.1 | 188.4 | 211 | 168.9 | 94.6 | 105.8 | 84.7 | 47.3 | 53 | 42.3 | 23.5 | 26.4 | 21 | 11.5 | 13 | 10.3 |
| 3.05 | 171.3 | 196.1 | 145 | 92.8 | 103.4 | 83.1 | 46.8 | 52.3 | 41.8 | 23.4 | 26.5 | 20.9 | 11.5 | 12.9 | 10.2 |
| 3 | 104.4 | 125.5 | 83.6 | 60.5 | 73.2 | 49.2 | 42.1 | 48.6 | 33.3 | 22.9 | 25.6 | 20.5 | 11.4 | 12.8 | 10.2 |
| 2.95 | 45.8 | 58.9 | 35.2 | 30.9 | 37.9 | 24.9 | 20.4 | 24.5 | 16.9 | 15.3 | 21 | 11.9 | 11 | 12.3 | 9.9 |
| 2.9 | 22.9 | 26.8 | 19.4 | 15 | 18 | 12.5 | 10.9 | 13.2 | 8.9 | 7.9 | 9.20 | 6.7 | 5.9 | 7.3 | 4.8 |
| 2.85 | 12.7 | 15.1 | 10.6 | 8.5 | 10 | 7.2 | 5.8 | 6.8 | 4.9 | 4.2 | 5.1 | 3.5 | 3.2 | 3.8 | 2.7 |
| 2.8 | 7.7 | 9 | 6.6 | 4.8 | 5.6 | 4.1 | 3.3 | 3.8 | 2.8 | 2.3 | 2.7 | 1.9 | 1.7 | 2 | 1.4 |
| 2.75 | 5.5 | 6.6 | 4.6 | 3.2 | 3.8 | 2.7 | 1.9 | 2.3 | 1.6 | 1.3 | 1.5 | 1 | 0.8 | 1 | 0.7 |
| 2.7 | 3.8 | 4.8 | 2.9 | 2.1 | 2.6 | 1.7 | 1.2 | 1.5 | 1 | 0.7 | 0.9 | 0.5 | 0.4 | 0.5 | 0.3 |
| 2.65 | 2.1 | 3.1 | 1.2 | 1.1 | 1.6 | 0.7 | 0.6 | 0.9 | 0.4 | 0.3 | 0.5 | 0.2 | 0.1 | 0.2 | 0 |
| 2.6 | -0.3 | 0.7 | -1.3 | -0.2 | 0.3 | -0.7 | -0.2 | 0.1 | -0.4 | -0.1 | 0 | -0.3 | -0.1 | 0 | -0.2 |

AVG=60.5 months, MAX=73.2, MIN=49.2

SYSTEM AND METHOD FOR DETERMINING REMAINING BATTERY LIFE FOR AN IMPLANTABLE MEDICAL DEVICE

FIELD OF THE INVENTION

The present invention relates generally to the field of implantable medical devices (IMDs), and more particularly to a system and method for determining an estimate of remaining battery life of the IMD.

BACKGROUND OF THE INVENTION

At present, a wide variety of IMDs are commercially released or proposed for clinical implantation that are programmable in a variety of operating modes and are interrogatable using RF telemetry transmissions. Such medical devices include implantable cardiac pacemakers, cardioverter/defibrillators, cardiomyostimulators, pacemaker/cardioverter/defibrillators, drug delivery systems, cardiac and other physiologic monitors, electrical stimulators including nerve and muscle stimulators, deep brain stimulators, and cochlear implants, and heart assist devices or pumps, etc. Most such IMDs comprise electronic circuitry and an IMD battery that provides power to the electronic circuitry and that depletes in energy over time. Therefore, it is necessary to monitor the state of the battery in such IMDs so that the IMD can be replaced before the battery depletes to a state that renders the IMD inoperable.

Typically, certain therapy delivery and monitoring operational modes and parameters of the IMD are altered temporarily or chronically in a non-invasive (i.e. non-surgical) manner using downlink telemetry transmission from an external programmer of programming and interrogation commands (herein referred to as "downlink telemetry data"). Moreover, a wide variety of real time and stored physiologic data and non-physiologic data particular to the patient (referred to collectively herein as "patient data") can be uplink telemetry transmitted by the IMD to the programmer in response to a downlink telemetry transmitted interrogation command. Other device specific data, including programmed operating modes and parameter values, device state data, and particularly the battery voltage and/or impedance, can also be uplink telemetry transmitted by the IMD to the programmer in response to a downlink telemetry transmitted interrogation command. Such device specific data and patient data are collectively referred to as "uplink telemetry data".

Since it is often extremely critical for patients' well-being that IMDs do not cease operating, it is common for IMDs to monitor the level of battery depletion and to provide some indication when the depletion reaches a level at which the battery should be replaced. Pacing implantable pulse generators (IPGs) manufactured by Medtronic, Inc., for example, typically monitor battery energy and depletion and develop an "elective replacement indicator" (ERI) when the battery depletion reaches a level such that replacement will soon be needed to avoid further depletion to a battery "end of life" (EOL) condition. Operating circuitry in the pacing IPG typically responds to issuance of an ERI by switching or deactivating operating modes to lower power consumption in order to maximize the ERI-to-EOL interval. For example, internal diagnostic functions and advanced rate-response functions may be discontinued upon issuance of ERI. Additionally, pacing IPG may switch to a relatively low rate, demand pacing mode upon issuance of the ERI as described in commonly assigned U.S. Pat. Nos. 4,390,020, 5,370,668, and 6,016,448, for example. Moreover, the battery impedance, voltage and other indicators of the level of battery depletion can be interrogated during a telemetry session and uplink telemetry transmitted for display and analysis employing the programmer as described above.

In pacing IPGs that monitor battery depletion and provide an ERI, it is important that there be sufficient time between triggering of ERI and complete battery depletion (battery EOL), so that the pacemaker will continue to operate for at least some minimum amount of time after issuance of an ERI. In this way, the physician will have sufficient time to take appropriate action, e.g., to replace the device before battery EOL. At the same time, it is also important not to trigger ERI too early or due to transient faults, since it is desirable that the sudden operational changes associated with ERI not be made until it is actually necessary to do so. Consequently, efforts have been undertaken to avoid issuing an ERI when transient battery states occur that could trigger issuance of the ERI as set forth in the above-referenced '668 patent, for example, or to derive multi-level ERI indicators as set forth in the above-referenced '448 patent, for example.

In addition, efforts have been made to derive and provide the physician with a reliable estimate of remaining battery life between the ERI and EOL, sometimes characterized as an elective replacement time (ERT) or a recommended replacement time (RRT) as described in U.S. Pat. No. 5,620,474, for example.

Lithium-Iodine batteries are among the most commonly used power sources in pacing IPGs, and much has come to be known about their depletion characteristics. In particular, it is well known in the art that the output voltage from Lithium-Iodine batteries is relatively flat during early stages of depletion, but drops off rather sharply before EOL. This is due in part to the internal resistance of Lithium-Iodine batteries, which is relatively linear as a function of energy depletion until near EOL, at which time the resistance curve exhibits a "knee" where internal resistance begins to rise rapidly. The voltage, capacitance, and impedance characteristics of various Lithium-Iodine cells exhibited over their life times from beginning of life (BOL) are described further in commonly assigned U.S. Pat. No. 5,391,193 and in the above-referenced '668 and '448 patents, for example.

The Lithium-iodine battery impedance is history-dependent, i.e. the battery impedance at a point in time following a high rate of discharge of the battery differs from the battery impedance that would be exhibited at the same point in time at a lower rate of discharge. Thus, it is necessary to track the accumulated discharge or current drain that the battery is subjected to from BOL in order to predict the time to ERT or RRT with less uncertainty.

The prior art fairly consistently observes that it is necessary in some way to employ all of these factors in assessing the state of discharge of the Lithium-Iodine battery due to its discharge characteristics However, the use of voltage measurement alone was suggested in U.S. Pat. No. 4,313,079 whereby a battery depletion monitor employs a CMOS inverter to compare the battery voltage to a reference voltage. When the reference voltage exceeds the measured battery voltage, the inverter changes state to indicate battery depletion. However, the loaded terminal voltage of a Lithium-Iodine battery can vary significantly depending upon current consumption due to the internal impedance characteristics discussed above. Thus, if relatively little current is drawn from the Lithium-Iodine battery for a period of time when the battery is nearing but has not reached the ERI point, a sudden prolonged period of high demand on the battery may cause a situation in which too little time is available between the ERI and EOL of the battery. For a particular pacing IPG and lead combination in a given patient, there will be a variation in the effective load on the Lithium-Iodine battery, and a resulting variation in the overall current drain.

Accordingly, if ERI is predicated upon sensing the voltage of the Lithium-Iodine battery and detecting when it drops below a certain level, there can be very little assurance that the level chosen will correspond to the knee of the internal resistance curve. It is therefore necessary to select a high threshold voltage and that unduly shortens the useful life of the pacing IPG.

Many other approaches have been described in the prior art for estimating the remaining life until ERI from measured Lithium-Iodine battery voltage and impedance and also including data related to the operating history of the IMD, e.g., cumulative delivered pacing pulses in the case of pacemakers as described in the above-referenced '193, and '448 patents and in U.S. Pat. No. 5,193,538, for example.

More recently developed, implantable grade, Lithium-Carbon Monofluoride or $Li(CF_x)_n$ batteries have been introduced for use in powering IMDs. High-rate hybrid cathode batteries and cells comprising lithium anodes and cathodes containing mixtures of various types of silver vanadium oxide (SVO) or "combination silver vanadium oxide" (CSVO) and $(CF_x)_n$, are disclosed in U.S. Pat. Nos. 5,114, 810, 5,180,642, 5,624,767, 5,639,577, 5,667,916, 5,221,453, 5,439,760, 5,306,581 and 5,895,733.

Commonly assigned U.S. Pat. No. 6,157,531 describes embodiments of batteries having lithium anodes, an electrolyte that comprises about 1.0 M $LiBF_4$, and a cathode that comprises about 90% by weight active materials, i.e., 90% by weight of a mixture of $(CF_x)_n$ and SVO, about 7% by weight polymer binder and about 3% conductive carbon. It is suggested therein that such batteries should be cathode limited to permit accurate, reliable prediction of battery end-of-life on the basis of observing voltage discharge curves since the discharge characteristics of cathode-limited cells are relatively uniform.

However, the determination of the remaining longevity estimate (RLE), that is the time remaining until battery ERI, is not directly possible simply employing direct measurement of battery voltage and extrapolating the remaining battery life from the measured voltage. It is necessary to take into account current consumption factors.

Moreover, it would be desirable to provide an RLE that becomes more and more accurate as battery voltage decreases to assure the physician that the indicated RLE does not overestimate the actual RLE and endanger the patient. The degree of accuracy of the RLE of a fresh and not defective battery at BOL determined at the time of implant would typically be less important than the degree of accuracy of the RLE of a battery approaching EOL.

SUMMARY OF THE INVENTION

The present invention utilizes the characteristic features of the battery discharge curves of IMD batteries that are reproducible and predictable under all current drain operating conditions encountered in use of the IMD. These characteristic features include, but are not limited to, a predictable voltage level at a given current drain at all depths of discharge.

The present invention also utilizes an understanding of the drain requirements of the IMD circuitry that are predictable.

Third, the cumulative effect of battery, circuit and lead tolerances and errors must be understood and modeled so as to provide valid statistical models for IMD longevity. Under these conditions, the RLE of the IMD battery can be accurately predicted at any point in time from the measured battery voltage and measured or estimated current drain at that time.

In accordance with a preferred embodiment, the IMD measures IMD battery voltage periodically, e.g., every 3 hours, averages the results of every 24 consecutive voltage measurements to produce a running average battery voltage measurement, and maintains the running average battery voltage measurement in IMD memory. The IMD also accumulates battery energy use data, e.g., the count of therapy delivery, e.g., pacing pulses delivered by a pacing IMD, or physiologic monitoring incidents or the like, collectively referred to as an incident count. Each such incident consumes a known battery energy bolus, e.g., the amount of battery energy consumed each time a pacing pulse having known pacing parameters is delivered.

In a telemetry session, a programmer interrogates programmed parameter information and diagnostic data of the IMD including the average battery voltage measurement and current drain indicating data. Current drain indicating data includes background or static or quiescent current drain, e.g., the average energy consumed by the circuitry while monitoring a physiologic parameter of the body, combined with episodic current drain incidents, e.g., delivery of a current consuming therapy through a therapy delivery channel to the body or consumption of energy in monitoring a physiologic parameter. The programmer commands the IMD to initiate measurements of the impedance of the therapy delivery or physiologic monitoring channel. The quiescent current drain can be assumed to be a fixed value determined by the design of the IMD circuitry. The current drain incidents can also be estimated from characteristic operations of the IMD or can be derived from accumulated incident data over a relatively recent time period.

In a pacing system, the delivered pace pulse count of all pacing channels over a predetermined time period, e.g., 72 hours, and the current programmed pacing parameters of each pacing channel are uplink telemetry transmitted to the external programmer from the IMD memory. In the pacing context, the impedance at the output of each pacing pulse generator in each pacing channel is measured by the IMD and uplink telemetry transmitted. Alternatively, the channel impedance may be periodically determined and stored in IMD memory by the IMD itself and uplink telemetry transmitted to the programmer upon receipt of the downlink telemetry transmitted interrogation command.

The programmer computes an "estimated past current drain" (EPCD) as a function of the measured channel impedance and the incident data including the energy consumed in each incident and the incident count. The EPCD is the estimated average current drain from the time of the most recent past computation to the present time of computation or a shorter time period. It is not necessary to account for or calculate current accumulated current drain from BOL but only a recent average current drain.

The programmer then computes the RLE (i.e., time "T" remaining to ERI) based on the average battery voltage and EPCD. In this case, ERI represents a depleted battery voltage on the characteristic battery discharge curve that precedes further discharge to the EOL voltage that is incapable of adequately powering the IMD circuitry by a predictable number of weeks.

A minimum "tolerance interval" representing a minimum percentile RLE (T_min-past) and a maximum tolerance interval representing a maximum percentile RLE (T_max-past) estimates, as well as the average RLE (T_avg-past), are also computed. The minimum percentile RLE is the T_min-past that represents the RLE during which X % of IMD batteries of the type will discharge to the ERI voltage, where X % can be 5% or any other selected minimum percentage. The maximum percentile RLE is the T_max-past that represents the RLE during which Y % of IMD batteries of the type will discharge to the ERI voltage where Y % can be 95% or any other selected maximum percentage. The computation of T_min-past, T_max-past, and T_avg-past is preferably accomplished using three, fixed 2-dimensional lookup tables, whose indices are battery voltage and EPCD in micro-amps.

The T_min-past, T_-max-past, and the T_avg-past lookup tables preferably represent a plurality of characteristic, predictable battery discharge curves at a respective plurality of EPCD values. The intersection of the EPCD and the battery voltage may fall between plotted look-up table values, and in that case, an interpolation algorithm is invoked to interpolate the T_min-past RLE, T_max-past RLE, and the T_avg-past RLE.

If the IMD is reprogrammed during the current follow-up to adjust pacing energy of future pacing until the next follow-up, then an "estimated future current drain" (EFCD), that is likely to be different from the EPCD, is computed. The RLEs are scaled according to the ratio of EPCD to EFCD before being displayed to the user:

$$T_{min\text{-}future} = T_{min\text{-}past} \cdot (EPCD/EFCD)$$

$$T_{max\text{-}future} = T_{max\text{-}past} \cdot (EPCD/EFCD)$$

$$T\_avg\text{-}future = T\_avg\text{-}past \cdot (EPCD/EFCD)$$

Note that this scaling method depends on two assumptions about the battery, which are 1) independence of capacity at ERI with respect to current drain, and 2) negligible self-discharge. The scaling equation can be enhanced to accommodate batteries for which these assumptions do not hold.

Thus, preferably maximum, minimum and average RLEs of an IMD battery are determined as a function of battery voltage and EPCD, and the EFCD, if different from the EPCD. The maximum, minimum and average RLEs become more accurate as they shorten as battery voltage decreases, increasing the physician's confidence in the accuracy of the RLE.

While the maximum, minimum and average RLEs could all be determined within the IMD and uplink telemetry transmitted upon receipt of an interrogation command if sufficient computing power and memory were provided, it is preferable at the present time to share the computation burden and allocate resources between the IMD and an external programmer typically operated by the physician to initiate determination of the maximum, minimum and average RLEs periodically.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 6 is an exemplary look-up table of T_min-past, T_max-past, and T_avg-past RLEs based upon EPCD and measured battery voltage.

DETAILED DESCRIPTION OF THE PREFERRED EMBODIMENTS OF THE INVENTION

The monotonically decreasing shape of the discharge curve and the high reproducibility of the discharge curve for LI$(CF_x)_n$ SVO/CSVO hybrid batteries of the type described above make them highly suitable for use in the practice of the present invention. The present invention can be implemented in any IMD that is powered by such a battery or equivalent and has uplink and downlink telemetry capabilities. At present, a wide variety of IMDs are commercially released or proposed for clinical implantation that rely upon a battery of this type. Such medical devices include implantable cardiac pacemakers as well as ICDs, pacemaker-cardioverter-defibrillators, drug delivery pumps, cardiomyostimulators, nerve and muscle stimulators, deep brain stimulators, cochlear implants, artificial hearts, cardiac and other physiologic monitors, etc.

Such IMDs impose a quiescent current drain on the battery and periodically imposes an episodic current drain on the battery in an energy consuming incident including one or more of delivery of a therapy through a therapy delivery channel or monitoring a physiologic condition through a monitoring channel. The quiescent and episodic current drain consuming battery energy that cumulatively causes battery voltage to drop to a defined ERI battery voltage. The following description is of a pacing system or pacemaker IMD, wherein the episodic current drain comprises the delivery of pacing pulses through one or a plurality of pacing channels, each pacing pulse delivering a bolus of energy depleting the battery and characterized as an "$I_{therapy}$".

Figure 1:
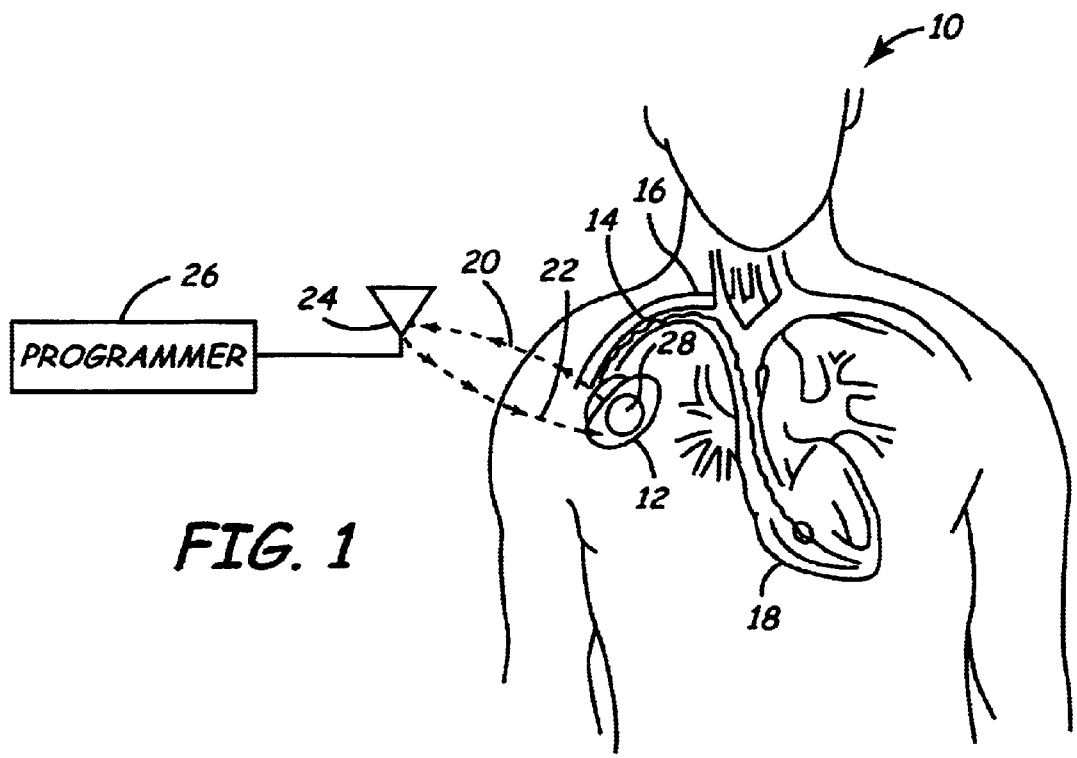
FIG. 1 is a simplified schematic view of uplink and downlink telemetry transmissions between an exemplary IMD implanted in a patient's body and an external programmer.
Figure 3:
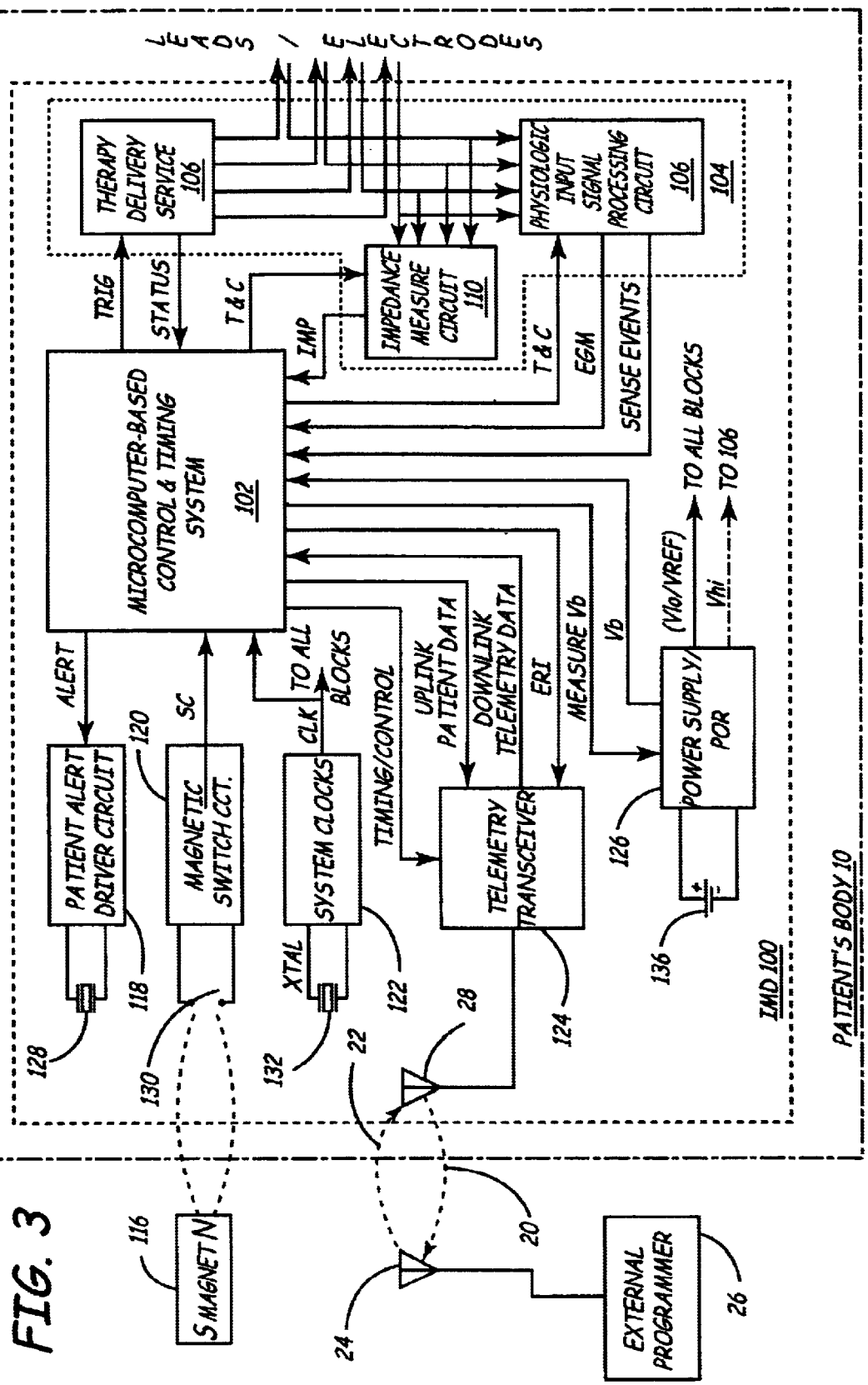
FIG. 3 is a block diagram of the system architecture of an exemplary IMD that incorporates delivery of a therapy and/or physiologic input signal processing in which the telemetry system of the present invention is incorporated.

FIG. 1 illustrates bi-directional telemetry communication between an external programmer 26 and an IMD 100, e.g., a pacing system embodied in an ICD or cardiac pacemaker IPG 12, and an endocardial lead 14, in accordance with an illustrative embodiment of the present invention. The IPG 12 is implanted in the patient 10 beneath the patient's skin or muscle and is typically oriented parallel to the skin surface. The IPG 12 is electrically coupled to the heart 18 of the patient 10 through pace/sense or cardioversion/defibrillation electrodes and lead conductor(s) of at least one endocardial lead 14 coupled to the IPG connector in a manner known in the art. The IPG 12 contains a battery and an operating system powered by the battery that may employ a microcomputer or a digital state machine for timing and controlling device functions in accordance with a programmed operating mode. An exemplary operating system enclosed within IPG 12 is depicted in FIG. 3 and described further below.

When the IPG 12 provides cardiac pacing functions, its operating system memory registers in RAM for storing a variety of programmed-in operating mode and parameter values that are used by the operating system. The memory registers may also be used for storing patient data compiled from sensed cardiac activity and/or relating to device operating history or sensed physiologic parameters for telemetry out on receipt of downlink transmitted retrieval or interrogation command. The operating system also includes at least one pacing channel, comprising sense amplifiers for detecting cardiac signals and pulse generating output circuits for delivering pacing pulses to at least one heart chamber of the heart 18 through a pace/sense electrode pair and lead conductors. The operating system determines when and if pacing pulses will be delivered in the pacing channel. The pacing rate is preferably determined as a function of the determined requirements for cardiac output assessed from patient activity signals or other physiologic signals in a manner well known in the prior art. When the IPG 12 is an ICD, it includes one or more high power cardioversion/defibrillation output capacitor, electronic circuitry coupled to the sense amplifiers for detecting and discriminating pathologic and/or non-pathologic arrhythmias from one another and providing other functions, high voltage electronic charging circuitry for charging the output capacitor(s) from a battery voltage to a higher voltage, and electronic switching circuitry for dumping the charge built up on the output capacitor(s) through the cardioversion/defibrillation electrodes. Such a pacemaker or ICD IPG 12 is described in detail in commonly assigned U.S. Pat. Nos. 5,626,620 or 5,931,857, respectively.

The IPG operating system also includes telemetry circuitry and a telemetry antenna 28, which can take the form of a surface mounted antenna or an antenna enclosed within or mounted to the IPG connector. By way of background to place the present invention in context, the IPG telemetry system and functions that are employed in transmitting data used to determine the RLEs are first described as follows. The terms "telemeter", "telemetry transmission" and the like are intended to embrace any action and manner of communicating and conveying uplink telemetry (UT) and downlink telemetry (DT) data between the IPG 12 and any external monitoring device or programmer 26 in the UT direction and the DT direction, respectively. For convenience of description, the preferred embodiments are described as follows using RF downlink telemetry (DT) transmissions 22 and uplink telemetry (UT) transmissions 20.

DT and UT data packets are transmitted between the IPG RF telemetry antenna 28 within or on or extending from a surface of the IPG 12 and an external RF telemetry antenna 24 associated with the external programmer 26. In the UT transmission 20, the external RF telemetry antenna 24 operates as a telemetry receiver antenna, and the IPG RF telemetry antenna 28 operates as a telemetry transmitter antenna. Conversely, in the DT transmission 22, the external RF telemetry antenna 24 operates as a telemetry transmitter antenna, and the IPG RF telemetry antenna 28 operates as a telemetry receiver antenna.

Figure 2:
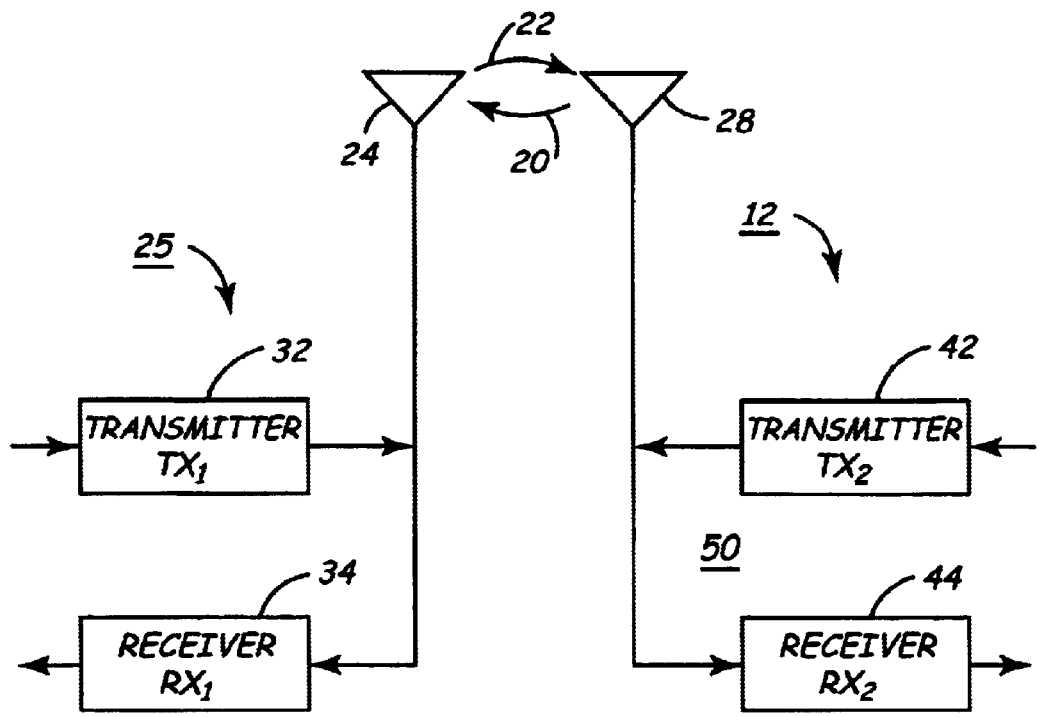
FIG. 2 is a simplified block diagram of major functional uplink and downlink telemetry transmission functions of the external programmer and IMD of FIG. 1.

FIG. 2 illustrates certain of the functional telemetry transmission blocks of the external programmer 26 and IPG 12 of FIG. 1. The external RF telemetry antenna 24 within the programmer 26 is coupled to a telemetry transceiver comprising a telemetry transmitter 32 and telemetry receiver 34. The programmer telemetry transmitter 32 and telemetry receiver 34 are coupled to control circuitry and registers operated under the control of a microcomputer and software as described in commonly assigned U.S. Pat. No. 5,843,139, for example. Similarly, within the IPG 12, the IPG RF telemetry antenna 28 is coupled to a telemetry transceiver comprising a telemetry transmitter 42 and telemetry receiver 44.

To initiate UT transmission 20, the telemetry transmitter 32 in external programmer 26 is enabled in response to a user input to generate an INTERROGATE command in a DT transmission 22. The INTERROGATE command is received and demodulated in receiver 44 and applied to an input of the IMD central processing unit (CPU), e.g. a microcomputer (not shown). The IMD microcomputer responds by forwarding the requested patient data to the transmitter 42 that generates the encoded uplink telemetry transmission 20.

The uplink and downlink telemetry transmissions 20 and 22 follow a telemetry protocol that formulates, transmits and demodulates uplink and downlink telemetry data packets each comprising a bit stream of FSK modulated data bits. The data packets are formulated of an FSK data bit stream with a preamble, data and error checking data bits. A carrier frequency centered in a 300 kHz band between 402 MHz and 405 MHz is modulated in frequency or frequency shifted up representing a data bit "1" or shifted down to represent the data bit "0". Each UT and DT transmission 20 and 22 takes place during a respective uplink telemetry transmission time period and downlink telemetry transmission time period.

FIG. 3 depicts a system architecture of an exemplary IMD 100 implanted into a patient's body 10 that provides delivery of a therapy and/or physiologic input signal processing. The typical IMD 100 has a system architecture that is constructed about a microcomputer-based control and timing system, 102 which varies in sophistication and complexity depending upon the type and functional features incorporated therein. The functions of microcomputer-based IMD control and timing system 102 are controlled by firmware and programmed software algorithms stored in RAM and ROM including PROM and EEPROM and are carried out using a CPU, ALU, etc., of a typical microprocessor core architecture. The microcomputer-based IMD control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of IMD 100 can be accomplished with dedicated circuit hardware or state machine logic rather than a programmed microcomputer.

The IMD 100 also typically includes patient interface circuitry 104 for receiving signals from sensors or electrodes located at specific sites of a patient's body 10 and/or delivering a therapy to a site of the patient's body 10. The typical patient interface circuitry 104 therefore comprises a therapy delivery system 106 and a physiologic input signal processing circuit 108 or simply one or the other. In accordance with the present invention, a further lead impedance measuring circuit 110 is included in patient interface circuitry 104 that is selectively enabled to measure the impedance in each therapy delivery channel or physiologic sensor channel. In the context of a pacing system, the impedance at the output of a pacing pulse generator coupled through a pacing lead with pace/sense electrode pairs comprises a pacing therapy delivery channel.

The therapy delivery system 106 can be configured to deliver electrical stimulation to the body, e.g., cardioversion/defibrillation shocks and/or cardiac pacing pulses delivered to the heart, or other electrical stimulation delivered to the brain, other organs, selected nerves, the spinal column, the cochlea, or muscle groups, including skeletal muscle wrapped about the heart. Alternatively, the therapy delivery system 106 can be configured as a drug pump delivering drugs into organs for therapeutic treatment or into the spinal column for pain relief. Or therapy delivery system 106 can be configured to operate an implantable heart assist device or pump implanted in patients awaiting a heart transplant operation.

It will be understood that most therapy delivery IMDs 100 also have a physiologic input signal processing circuit 108 that processes physiologic signals that are used to trigger or modulate therapy delivery and are stored as physiologic signal data for later retrieval as described above. The physiologic input signal processing circuit 108 is coupled to electrical signal sense electrodes and/or physiologic sensors on or in the housing of the IMD 100 or situated at sites distanced from the IMD housing, typically in distal portions of elongated leads. The sensors or electrodes located outside the housing are coupled by conductors to feedthrough pins of feedthroughs extending through the housing wall. Certain physiologic sensors or sense electrodes can be mounted to a connector assembly so that the conductors are quite short. Typically, however, the conductors include the elongated conductors of leads extending to the remotely situated physiologic sensors and sense electrodes.

The IMD 100 can comprise an implantable cardiac monitor without a therapy delivery system 106, e.g., an implantable EGM monitor for recording the cardiac electrogram from electrodes remote from the heart as disclosed in commonly assigned U.S. Pat. No. 5,331,966 and PCT publication WO 98/02209. Alternatively, the IMD 100 can comprise an implantable hemodynamic monitor (IHM) for recording cardiac electrogram and other physiologic sensor derived signals, e.g., one or more of blood pressure, blood gases, temperature, electrical impedance of the heart and/or chest, and patient activity. The Medtronic® REVEAL® Insertable Loop Recorder having spaced housing EGM electrodes is an example of the former, and the Medtronic® CHRONICLE® IHM coupled with a capacitive pressure and temperature sensing lead and EGM sense electrodes of the type described in commonly assigned U.S. Pat. No. 5,564,434 is an example of the latter.

These are merely exemplary configurations of IMD 100, therapy delivery system 106, and physiologic input signal processing circuit 108 for therapy delivery and/or monitoring. In all cases, the micro-computer-based control and timing system 102 governs all operating functions employing an appropriate, programmable operating algorithm. FIG. 3 also depicts other typical components common to an IMD 100 in any of these therapy delivery and/or monitoring configurations.

Virtually all current electronic IMD circuitry employs clocked CMOS digital logic ICs that require a clock signal CLK provided by a piezoelectric crystal 132 and system clock 122 coupled thereto. In FIG. 1, each CLK signal generated by system clock 122 is routed to all applicable clocked logic via a clock tree 138. The system clock 122 provides one or more fixed frequency CLK signal that is independent of the battery voltage over an operating battery voltage range for system timing and control functions and in formatting uplink telemetry signal transmissions in the telemetry I/O circuit 124.

In the IMD 100, uplink and downlink telemetry capabilities are provided to enable communication with either a remotely located external medical device or a more proximal medical device on the patient's body or another IMD in the patient's body as described above with respect to FIGS. 1 and 2.

The RAM registers may be used for storing patient data comprising physiologic patient data compiled from sensed cardiac activity or sensed physiologic parameters and non-physiologic patient data as well as device specific data relating to device operating history for uplink telemetry transmission on receipt of a retrieval or interrogation instruction via a downlink telemetry transmission. The criteria for triggering such patient data storage can also be programmed in via downlink telemetry transmitted instructions and parameter values The physiologic data storage is either triggered on a periodic basis or by detection logic within the physiologic input signal processing circuit 108 upon satisfaction of certain programmed-in event detection criteria.

In some cases, the IMD 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted IMD 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later initiated telemetry session.

In addition, real-time generated physiologic patient data can be transmitted by uplink RF telemetry from the IMD 100 to the external programmer or other remote medical device 26 in response to a downlink telemetry transmitted interrogation command. The real-time physiologic data typically includes real time sampled signal levels, e.g., intracardiac electrocardiogram amplitude values, and sensor output signals.

The non-physiologic patient data that can be transmitted by uplink RF telemetry from the IMD 100 to the external programmer or other remote medical device 26 includes currently programmed device operating modes and parameter values, battery condition, device ID, patient ID, implantation dates, device programming history, real time event markers, and the like. In the context of implantable pacemakers and ICDs, such device specific data includes programmed sense amplifier sensitivity, pacing or cardioversion pulse amplitude, energy, and pulse width, pacing or cardioversion lead impedance for each pacing or cardioversion channel, and accumulated statistics related to device performance, e.g., data related to detected arrhythmia episodes and applied therapies and/or the number of pacing pulses delivered.

As described above, all current IMDs rely upon a source of electrical energy to power the IMD operating system including the circuitry of IMD 100 and to power any electromechanical devices, e.g., valves, pumps, etc. of a substance delivery IMD, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an ERI signal, and, in the case of an ICD, high voltage power Vhi to the therapy delivery system 106. Not all of the conventional interconnections of these voltages and signals are shown in FIG. 1

In addition, in certain IMDs, an audible patient alert warning or message is generated by a transducer 128 when driven by a patient alert driver 118 to advise of device operations, battery power level, e.g., issuance of the ERI, or a monitored patient condition. In ICDs, the patient may be warned of the detection of a malignant tachyarrhythmia and the imminent delivery of a cardioversion/defibrillation shock to enable the patient to assume a resting position prior to delivery.

Figure 8:
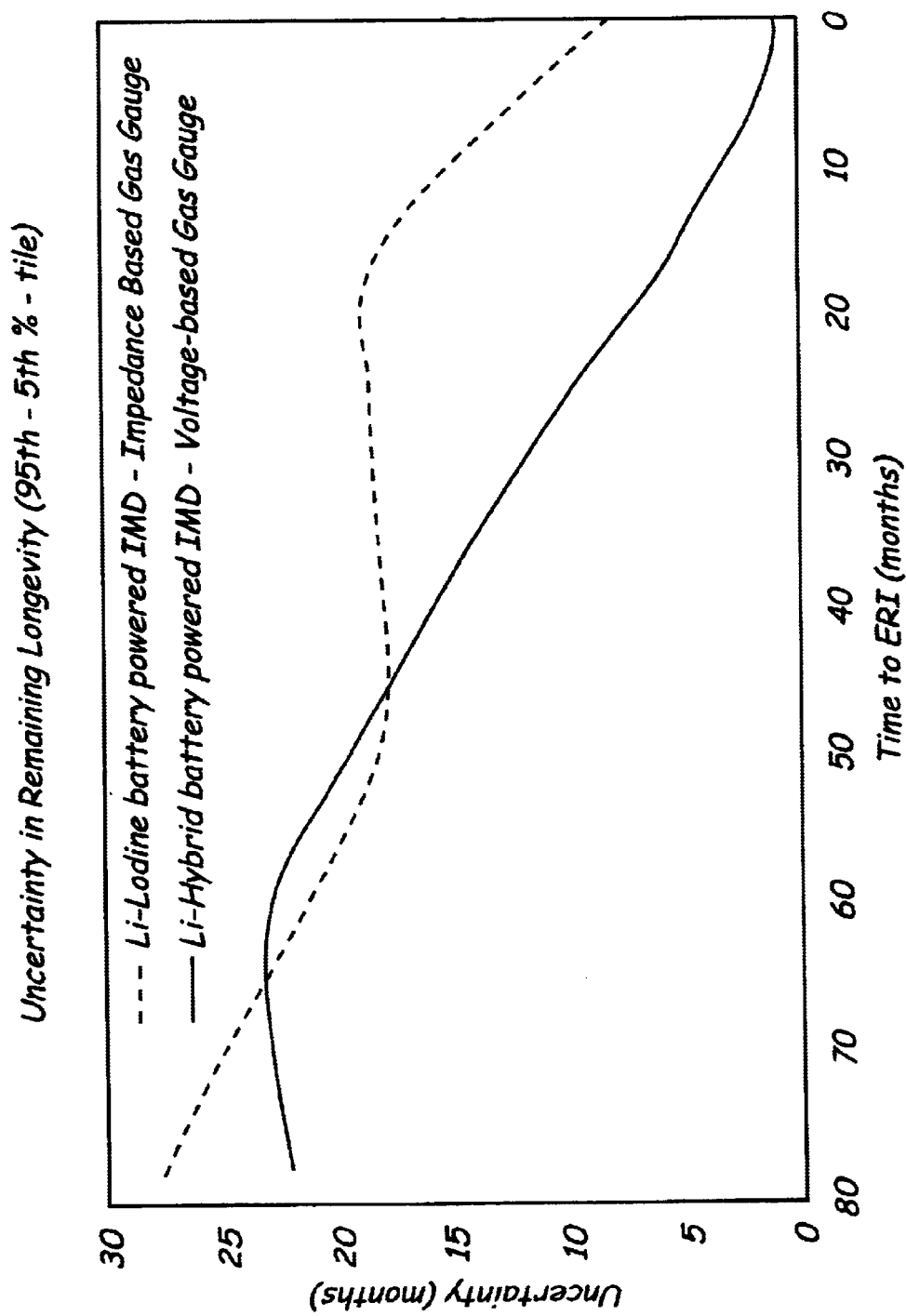
FIG. 8 is chart showing that the uncertainty in the RLE expressed in months diminishes as EOL is approached in IMDs powered by LI $(CF_x)_n$ SVO/CSVO hybrid batteries, whereas the uncertainty in the RLE increases in IMDs powered by Lithium-Iodine batteries.

In accordance with the present invention, the battery 136 exhibits a monotonic voltage drop as shown in FIG. 8 between the beginning-of-life voltage and the end-of-life voltage when an ERI is generated, e.g., a Li/CFx/CSVO battery. Preferably, the battery 136 has a lithium anode, a cathode comprising 27% by wt. CSVO, 63% by wt $CF_x$, 7% by wt PTFE & 3% by wt. carbon black and an electrolyte of 1 M $LiBF_4$ in a blend of 60 vol % gamma-butyrolactone and 40 vol % of 1,2 dimethoxyethane. In terms of electrochemical equivalents, there are 8 equivalents of $CF_x$ per equivalent of CSVO.

The determination of RLE of battery 136 in accordance with the present invention takes into account the battery voltage Vb and estimated past and future current drain and derives maximum, minimum and average RLEs. The maximum, minimum and average RLEs become more accurate as battery voltage decreases more rapidly near ERI, increasing the physician's confidence in the accuracy of the RLE.

The maximum, minimum and average RLEs could all be determined within the IMD and uplink telemetry transmitted upon receipt of an interrogation command if sufficient computing power and memory are provided within the IMD 100. It is preferable at the present time to share the computation burden and allocate resources between the IMD 100 and an external programmer 26 typically operated by the physician to initiate determination of the maximum, minimum and average RLEs periodically as described in reference to the flow charts of FIGS. 4 and 5, the chart of FIG. 6, and the look-up table of FIG. 7. The method of the present invention illustrated in these figures is explained in the context of determining the RLEs of a pacemaker or pacing system of an ICD, for convenience.

Figure 4:
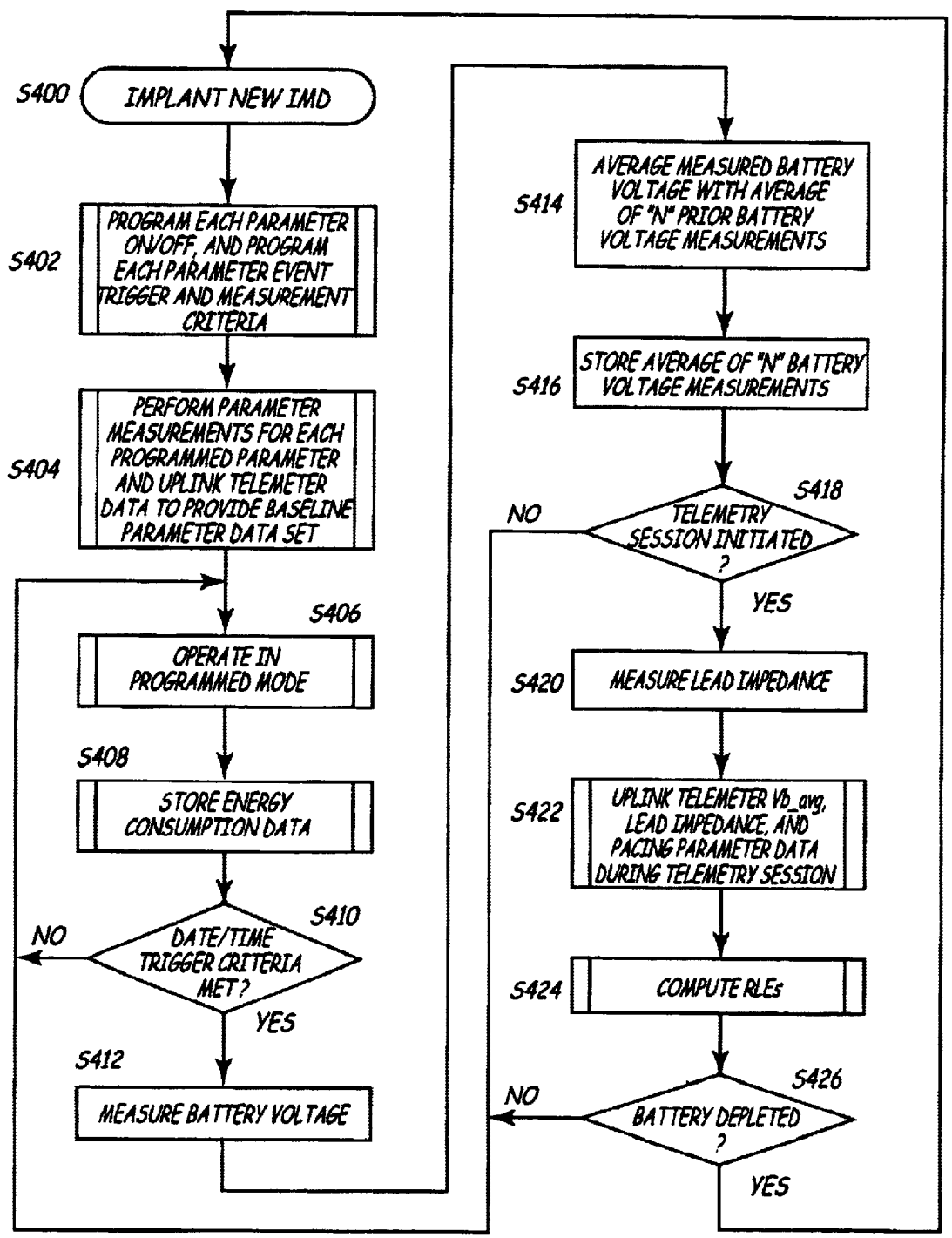
FIG. 4 is a flow chart illustrating the overall operation of an IMD and programmer of FIGS. 1–3 in normal operation implanted in a patient and during a telemetry session.

FIG. 4 illustrates the overall IMD and/or programmer function from the time of implantation (step S400) when initial programming (step 402) and baseline parameter measurements (step S404) are performed, through an implantation time period until a follow-up telemetry session (steps S406–S416), during each telemetry session (steps S418–S424), and the replacement of the IMD per step S426 if the IMD generated ERI indicates imminent battery EOL. Step S424 is expanded in the flow chart of FIG. 7, and the re-programming of any pacing parameters affecting current drain during the telemetry session is taken into account therein as described below. The present invention may be implemented into a versatile multi-chamber pacing system as described above or into a less comprehensive pacing system offering fewer programmable pacing parameters and operating modes.

In step S402, various measured parameters of the IMD can be programmed ON or OFF and event triggers and measurement criteria for such parameters that are programmed ON can programmed. The battery voltage measurement and the accumulation of pacing pulse counts would not normally be made programmable, but activity level and sensing parameters could be. In step S404, baseline parameter measurements are optionally performed for each programmed ON parameter to collect baseline or reference parameter data, to both store such data in IMD memory and to uplink telemeter the parameter data for observation by the physician and for use in programming the operating modes and parameter values. The initial and updated baseline parameter measurements can be stored in the IMD RAM memory and/or stored externally in a patient file maintained by the physician with a date and time stamp and other pertinent data, e.g. patient activity level measured by the activity signal processor circuit and patient heart rate, if measurable. The IMD 100 is then operated in its programmed mode in step S406.

During such operation, pacing pulses are delivered in each pacing channel in accordance with the pacing mode at the programmed pacing pulse width and pulse voltage for that channel, and the pacing pulse count for each channel is incremented each time a pace pulse is delivered in step S408.

A real time clock is timed out, and the IMD 100 measures IMD battery voltage Vb in step S412 periodically, e.g., every 3 hours, as determined in step S410. The measured battery voltage Vb is stored in a FIFO register in step S412 or simply directly averaged with the preceding "N" prior measured battery voltages (or fewer prior measured battery voltages until 24 are accumulated and/or averaged) in step S414. Preferably, N=24, and the resulting average measured battery voltage Vb_avg is stored in a memory register in step S416. Thus, the stored average measured battery voltage Vb_avg is updated with each new measurement made in step S412.

Deriving Vb_avg reduces fluctuations in battery voltage measurements due to time-varying factors that may temporarily influence battery voltage, including the patient's demand for pacing, the patient's varying activity level, possible diurnal or other variations in electrolytic levels which might influence pacing impedance, body temperature variations, etc. In addition, the battery voltage changes for a period of time until it stabilizes if the current drain on the battery changes when an IMD operating mode or parameter value is reprogrammed. Therefore, the battery voltage following reprogramming is an inaccurate indicator to be used to determine a RLE for a period of time following reprogramming.

Steps S412 through S416 are repeated each time that step S410 is satisfied. The data collection in steps S408 and S416 continues until the programmer initiated telemetry session of step S418 interrupts the process. The programmer interrogates programmed parameter information and diagnostic data including the average battery voltage measurement and current drain indicating data, e.g., delivered pacing pulse counts and the current programmed pacing parameters of each pacing channel of a pacing IMD, from the IMD memory. The programmer 26 commands the IMD 100 to initiate measurements of the pacing impedances at the output of each pacing pulse generator in each pacing channel in step S420 and to UT transmit the measured impedance data to the programmer 26 in step S422. Alternatively, the lead impedance may be periodically determined and stored in IMD memory by the IMD 100 and UT transmitted to the programmer 26 in step S422 upon receipt of the downlink telemetry transmitted interrogation command. However, the lead impedance measurement of step S420 is preferably made during the telemetry session initiated in step S418 for use by the programmer 26 in determining the T_min-past, T_max-past, and T_avg-past RLEs and T_min-future, T_max-future, and T_avg-future RLEs (if calculated) in step S424.

Figure 5:
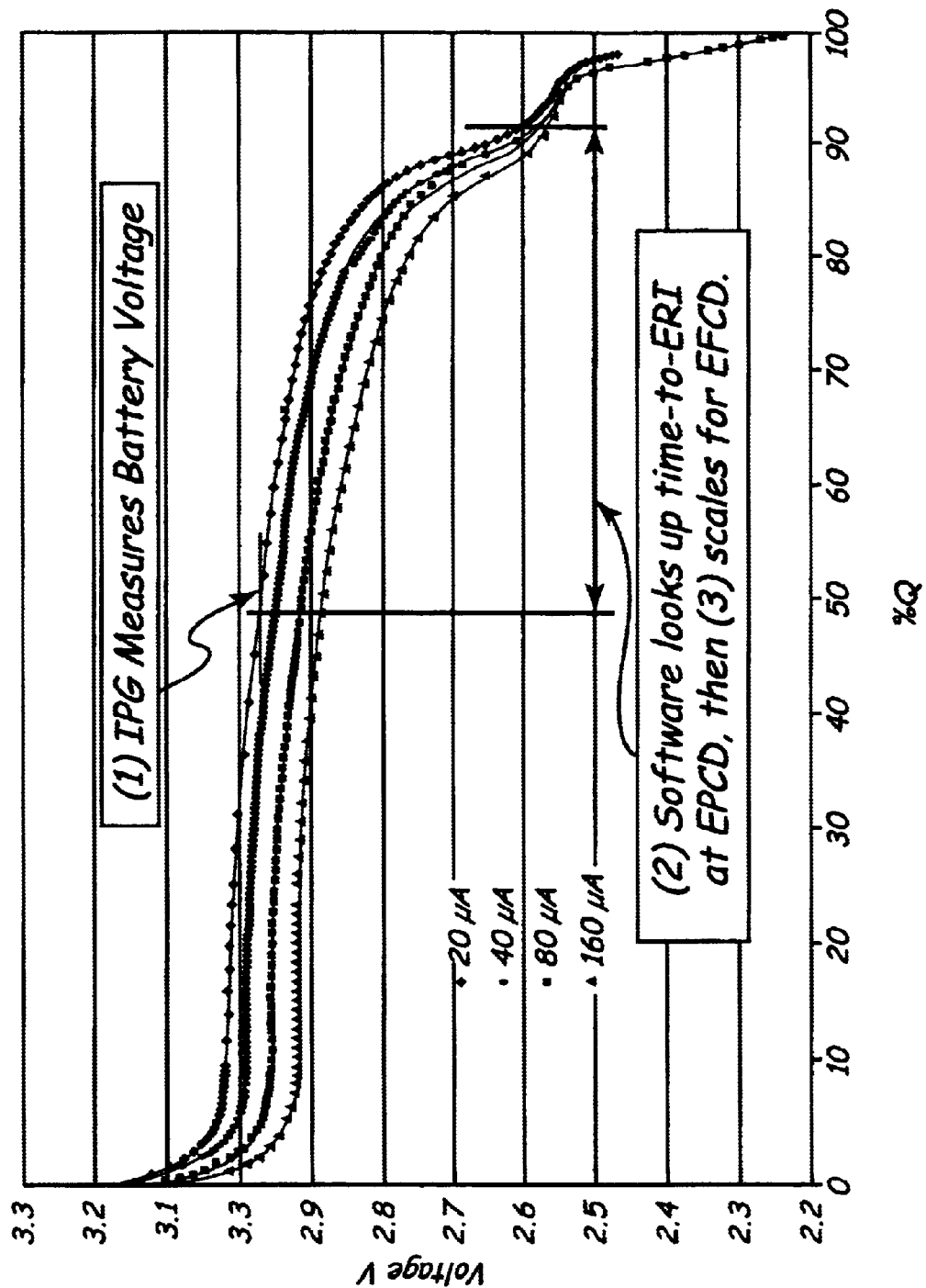
FIG. 5 is a chart illustrating a plurality of battery discharge curves at a plurality of EPCDs illustrating the relationship between a measured battery voltage at an EPCD that signifies the depth of discharge (% Q) of the IMD battery.

FIG. 5 is a graph illustrating a plurality of battery discharge curves at a plurality of EPCDs. Each curve shows the relationship between measured battery voltages and various depths of battery discharge (% Q) for a predetermined current drain level. The present invention utilizes the characteristic features of the battery discharge curves illustrated in FIG. 5 that are reproducible and predictable under all current drain operating conditions encountered in use of the IMD. These characteristic features include, but are not limited to, a predictable voltage level at a given current drain at all depths of discharge (% Q).

These battery discharge curves are derived empirically from long term battery discharge tests conducted at the differing current drains. The maximum IMD current drain of 160 $\mu$A approximates the current drain of the IMD if programmed to deliver a therapy at maximal energy, to the maximum number of therapy delivery channels, at the highest programmable rate, e.g. maximal energy pacing pulses delivered to multiple pacing channels at pacing upper rate limit through multiple pacing channels without inhibition by sensed events. The minimum IMD current drain of 20 $\mu$A approximates the current drain of the IMD in a quiescent state when it is not delivering any therapy, e.g., a pacing system that is fully inhibited or the like. The discharge curves at intermediate IMD current drains of 40 $\mu$A and 80 $\mu$A are also depicted. The ERI voltage in this instance is about 2.60 volts at 20 $\mu$A. The % Q can be directly related to the RLE at the EPCD.

FIG. 6 is an exemplary look-up table of T_min-past, T_max-past, and T_avg-past RLEs based upon EPCD and battery voltage. These RLEs are derived empirically from long term battery discharge studies at these current drains. Thus, it is determined empirically that the IMD battery of this type will discharge to ERI in the depicted number of months at each voltage and EPCD.

The T_min-past, T_max-past, and the T_avg-past RLEs are derived from such lookup tables. The combination of the EPCD and the battery voltage may fall between plotted look-up table values, and in that case, an interpolation algorithm is invoked to interpolate the T_min-past RLE, T_max-past RLE, and the T_avg-past RLE.

Figure 7:
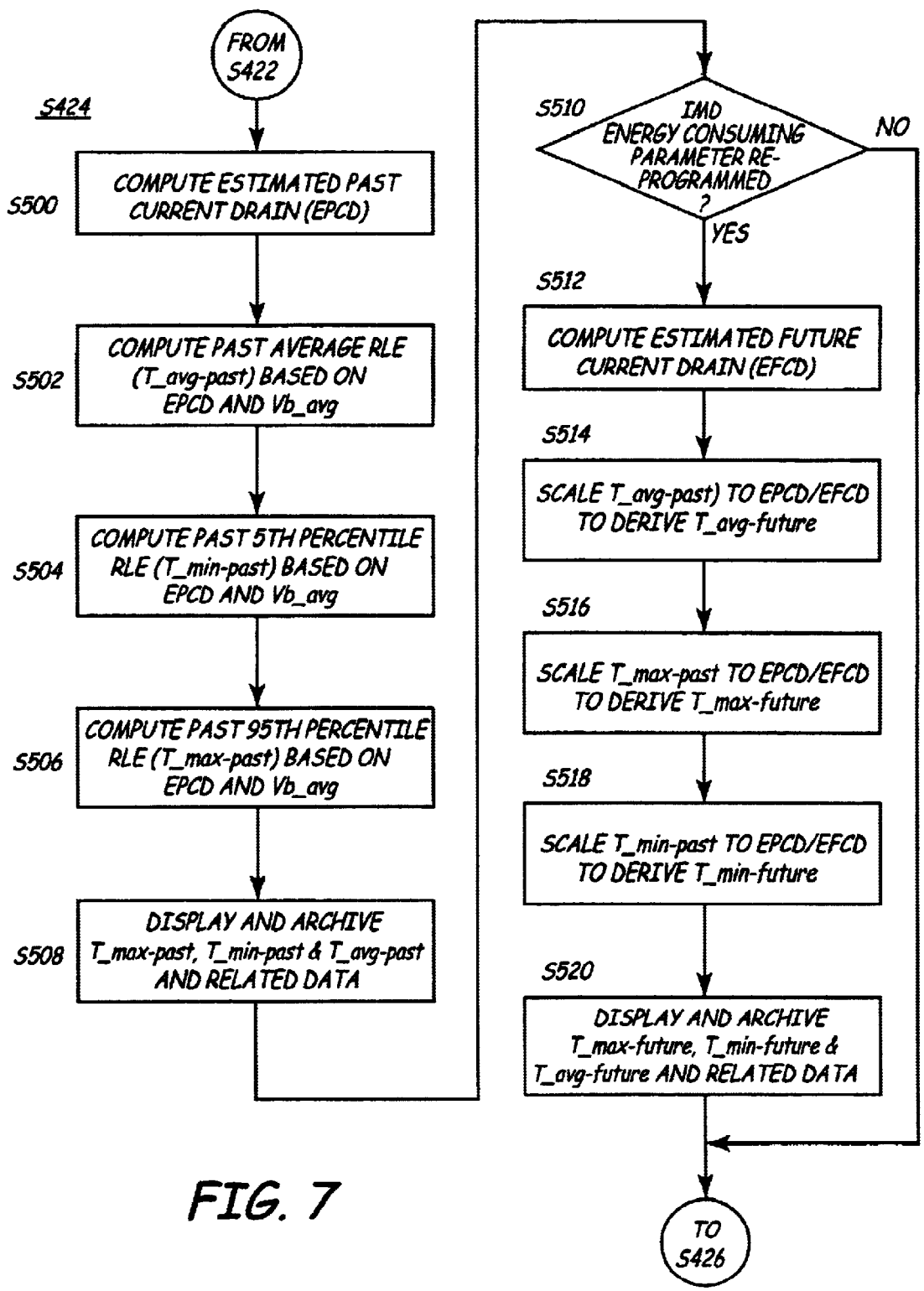
FIG. 7 is an expanded flow chart of step S424 FIG. 4 illustrating the determination of the minimum, maximum and average RLEs from battery voltage and other measured parameters.

FIG. 7 is an expanded flow chart of step S424 of FIG. 4 illustrating the computation and display of T_min-past, T_max-past, and T_avg-past RLEs in steps S500–S508 and, T_min-future, T_max-future, and T_avg-future RLEs in steps S510–S520, if a pacing parameter is reprogrammed. The average battery voltage Vb_avg, the pacing pulse width and amplitude parameters and measured lead impedance for each pacing channel that are UT transmitted to the programmer 26 in steps S420 and S422, as well as the programmer computed EPCD and EFCD (if computed), are all displayed to the physician in steps S508 and S520. This data is also preferably archived in steps S508 and S520 in a patient file database maintained by the programmer 26 or in a remotely accessed database. The data is also preferably DT transmitted and stored in an archival patient database file in RAM of the IMD 100, so that the same physician or another health care provider can access it at a later follow-up.

In step S500, the EPCD is computed based upon the measured lead impedance, pacing pulse parameters, and pacing pulse count for each pacing channel and then aggregated together, by adding the quiescent current drain ($I_{quiescent}$) of the IMD to the current drain related to therapy delivery ($I_{therapy}$):

$$I_{total} = I_{quiescent} + I_{therapy},$$

where:

$I_{quiescent}$=a constant representing the basic current drain of the IMD circuitry not including delivery of therapy stimuli, and $$I_{therapy} = \Sigma(I_{therapy\_1}, I_{therapy\_2}, \ldots, I_{therapy\_n})$$

where n=# of therapy channels, $I_{therapy\_i}$=average current drawn by therapy channel i.

In a preferred embodiment, the $I_{therapy\_i}$ for each pacing channel is computed as follows:

$$I_{therapy\_i} = C*(\text{Pacing\_pulse\_count})/(\text{Time})*V\_i/R\_i,$$

where:

C=the ratio of battery current drain to therapy current drain delivered to the patient. This ratio is a known function of the pacing pulse parameters, determined by the design of the stimulus generation circuitry;

Pacing_pulse_count=the count of pacing stimuli over a known period of time;

Time=said period of time;

V_i=average voltage delivered during each stimulus on channel i (either known based on pacing pulse parameters or measured during representative stimuli); and R_i=impedance of pacing channel i.

Steps S502, S504 and S506 are accomplished through reference to a look-up table 200 illustrated in FIG. 6 that is stored in RAM in programmer 26 for each type of applicable battery that IMDs programmed with the programmer 26 may have. The battery identification is made during interrogation and identification of the IMD 100 as is well known in the art. The operating system of the programmer 26 simply correlates the EPCD to the average battery voltage Vb_avg, selects the T_min-past, T_max-past, and T_avg-past RLEs from the look-up table 200, and displays and archives them in step S508. For example, if EPCD=20 micro-amps and Vb_avg=3.0 volts, then T_min-past=49.2 months, T_max-past=73.2 months, and T_avg-past=60.5 months.

Steps S512–S522 are followed if a pacing parameter in any pacing channel that affects the current drain is reprogrammed. The EFCD is calculated in step S512 using the re-programmed pacing parameters following the same process as is followed in step S500. The T_avg-future, T_min-future, and T_max-future RLEs are determined in steps S514, S516, and S518, by scaling the T_avg-past, T_min-past, and T_max-past RLEs, respectively, to the ratio of EPCD to EFCD before being displayed to the user:

$$T_{min\text{-}future} = T_{min\text{-}past} * (EPCD/EFCD)$$

$$T_{max\text{-}future} = T_{max\text{-}past} * (EPCD/EFCD)$$

$$T\_avg\text{-future} = T\_avg\text{-past} * (EPCD/EFCD)$$

Thus, the T_avg-future, T_min-future, and T_max-future RLEs exceed the T_avg-past, T_min-past, and T_max-past RLEs, respectively, if EPCD/EFCD>1.0 or are reduced if EPCD/EFCD<1.0.

The physician then sees the displayed T_min-past, T_max-past, and T_avg-past RLEs and T_min-future, T_max-future, and T_avg-future RLEs (if calculated) as well as the related data in step S426 and determines if the IMD battery is depleted sufficiently to warrant replacement of the IMD 100 in step S400 or to continue monitoring the currently implanted IMD 100 operating in the programmed mode of step S406. The scheduling of the next follow-up telemetry session can be correlated with the indicated RLE to the extent the physician is comfortable in doing so.

Advantageously, the accuracy of the calculated and displayed T_min-past, T_max-past, and T_avg-past RLEs and T_min-future, T_max-future, and T_avg-future RLEs (if calculated) increases as battery voltage declines toward the ERI battery voltage. FIG. 8 is chart showing that the uncertainty in the RLE expressed in months diminishes as EOL is approached in IMDs powered by $LI(CF_x)_n$ SVO/CSVO hybrid batteries, whereas the uncertainty in the RLE increases in IMDs powered by Lithium-Iodine batteries.

Thus, from the above it is apparent that the present invention has particular application to pacing system or pacemaker IMDs powered by batteries of the types described. The above-described algorithms may also be applied to any other therapy delivery or monitoring IMD where the EFCD and EPCD can be determined.

All patents and publications referenced herein are incorporated herein by reference in their entireties.

Although the invention has been described in detail with particular reference to a preferred embodiment and alternate embodiments thereof, it will be understood variations and modifications can be effected within the scope of the following claims. Such modifications may include substituting elements or components that perform substantially the same function in substantially the same way to achieve substantially the same result for those described herein.

What is claimed is:

1. In an implantable medical device (IMD) that is powered by a battery exhibiting a characteristic voltage drop at any given current drain from a beginning-of-life battery voltage to an elective replacement indicator battery voltage, the IMD imposing a quiescent current drain on the battery and periodically imposes an episodic current drain on the battery in an energy consuming incident including one or more of delivery of a therapy through a therapy delivery channel or monitoring a physiologic condition through a monitoring channel, the quiescent and episodic current drain consuming battery energy that cumulatively causes battery voltage to drop, a method of estimating the remaining life of the battery until battery voltage drops to the elective replacement indicator battery voltage comprising the steps of:

periodically measuring battery voltage and averaging a plurality of battery voltage measurements to derive an average measured battery voltage;

estimating the estimated past current drain of the IMD comprising an average of the sum of the quiescent current drain and the episodic current drain; and determining the estimated remaining longevity from the measured voltage and the estimated past current drain.

2. The method of claim 1, further comprising:

adjusting the battery energy bolus that will be consumed during each energy consuming incident or the frequency of occurrence of energy consuming incidents per unit of time occurring in the future; and the estimating step further comprises estimating an estimated future current drain for each channel as a function of the estimated past current drain and the adjusted battery energy bolus; and the determining step further comprises scaling the average remaining life estimate based upon estimated past current drain to the ratio of the estimated past current drain and the estimated future current drain to derive a scaled average remaining life estimate until the battery elective replacement interval voltage is reached.

3. The method of claim 1, wherein the estimating step further comprises estimating, from the estimated past current drain and the average measured battery voltage, a maximum percentile remaining life estimate of the time remaining during which a predetermined maximum percentage of batteries exhibiting the characteristic voltage drop of the battery voltage when subjected to the estimated past current drain of this type will fall to the elective replacement interval voltage.

4. The method of claim 3, further comprising:

adjusting the battery energy bolus that will be consumed during each energy consuming incident or the frequency of occurrence of energy consuming incidents per unit of time occurring in the future; and the estimating step further comprises estimating an estimated future current drain for each channel as a function of the estimated past current drain and the adjusted battery energy bolus; and the determining step further comprises scaling the maximum percentile remaining life estimate based upon estimated past current drain to the ratio of the estimated past current drain and the estimated future current drain to derive a scaled maximum percentile remaining life estimate until the battery elective replacement interval voltage is reached.

5. The method of claim 1, wherein the estimating step further comprises estimating, from the estimated past current drain and the average measured battery voltage, a 95th percentile remaining life estimate of the time remaining during which 95% of batteries exhibiting the characteristic voltage drop of the battery voltage when subjected to the estimated past current drain of this type will fall to the elective replacement interval voltage.

6. The method of claim 5, further comprising the step of:

adjusting the battery energy bolus that will be consumed during each energy consuming incident or the frequency of occurrence of energy consuming incidents per unit of time occurring in the future; and wherein:

the estimating step further comprises estimating an estimated future current drain for each channel as a function of the estimated past current drain and the adjusted battery energy bobs; and the determining step further comprises scaling the 95th percentile remaining life estimate based upon estimated past current drain to the ratio of the estimated past current drain arid the estimated future current drain to derive a scaled 95th percentile remaining life estimate until the battery elective replacement interval voltage is reached.

7. The method of claim 1, wherein the estimating step further comprises:

determining, from the estimated past current drain and the average measured battery voltage, a minimum percentile remaining life estimate of the time remaining during which a predetermined minimum percentage of batteries exhibiting the characteristic voltage drop of the battery voltage when subjected to the estimated past current drain of this type will fall to the elective replacement interval voltage.

8. The method of claim 5, further comprising the step of:

adjusting the battery energy bolus that will be consumed during each energy consuming incident or the frequency of occurrence of energy consuming incidents per unit of time occurring in the future; and wherein:
the estimating step further comprises estimating an estimated future current drain for each channel as a function of the estimated past current drain and the adjusted battery energy bolus; and
the determining step further comprises scaling the minimum percentile remaining life estimate based upon estimated past current drain to the ratio of the estimated past current drain and the estimated future current drain to derive a scaled minimum percentile remaining life estimate until the battery elective replacement interval voltage is reached.

9. The method of claim 1, wherein the estimating step further comprises:

determining, from the estimated past current drain and the average measured battery voltage, a 5th percentile remaining life estimate of the time remaining during which 5% of batteries exhibiting the characteristic voltage drop of the battery voltage when subjected to the estimated past current drain of this type will fall to the elective replacement interval voltage.

10. The method of claim 9, further comprising the step of:

adjusting the battery energy bolus that will be consumed during each energy consuming incident or the frequency of occurrence of energy consuming incidents per unit of time occurring in the future; and wherein:
the estimating step further comprises estimating an estimated future current drain for each channel as a function of the estimated past current drain and the adjusted battery energy bolus; and
the determining step further comprises scaling the 5th percentile remaining life estimate based upon estimated past current drain to the ratio of the estimated past current drain and the estimated future current drain to derive a scaled 5th percentile remaining life estimate until the battery elective replacement interval voltage is reached.

11. The method of claim 1, wherein:

the IMD comprises a cardiac pacing system that delivers pacing pulses in energy consuming incidents through a pacing lead and electrode and body tissue comprising a load having an impedance, whereby delivery of each pacing pulse consumes a predetermined bolus of energy, and
the estimating step further comprises measuring the impedance of the load.

12. The method of claim 1, wherein:

the IMD comprises an electrical stimulator that delivers stimulation pulses in energy consuming incidents through an electrode and body tissue comprising a load having an impedance, whereby delivery of each stimulation pulse consumes a predetermined bolus of energy, and
the estimating step further comprises measuring the impedance of the load.

13. An implantable medical device (IMD) that is powered by a battery exhibiting a characteristic voltage drop at any given current drain from a beginning-of-life battery voltage to an elective replacement indicator battery voltage, the IMD imposing a quiescent current drain on the battery and periodically imposes an episodic current drain on the battery in an energy consuming incident including one or more of delivery of a therapy through a therapy delivery channel or monitoring a physiologic condition through a monitoring channel, the quiescent and episodic current drain consuming battery energy that cumulatively causes battery voltage to drop, a method of estimating the remaining life of the battery until battery voltage drops to the elective replacement indicator battery voltage, the IMD further comprising:

means for periodically measuring battery voltage and averaging a plurality of battery voltage measurements to derive an average measured battery voltage;
estimating means for estimating the estimated past current drain of the IMD comprising an average of the sum of the quiescent current drain and episodic current drain; and
determining means for determining the estimated remaining longevity from the measured voltage and the estimated past current drain.

14. The IMD of claim 13, further comprising:

adjusting means for adjusting the battery energy bolus that will be consumed during each energy consuming incident or the frequency of occurrence of energy consuming incidents per unit of time occurring in the future; and wherein:
the estimating means further comprises means for estimating an estimated future current drain for each channel as a function of the estimated past current drain and the adjusted battery energy bolus; and
the determining means further comprises means for scaling the average remaining life estimate based upon estimated past current drain to the ratio of the estimated past current drain and the estimated future current drain to derive a scaled average remaining life estimate until the battery elective replacement interval voltage is reached.

15. The IMD of claim 13, wherein the estimating means further comprises means for determining, from the estimated past current drain and the average measured battery voltage, a maximum percentile remaining life estimate of the time remaining during which a maximum percentage of batteries exhibiting the characteristic voltage drop of the battery voltage when subjected to the estimated past current drain of this type will fall to the elective replacement interval voltage.

16. The IMD of claim 15, and further comprising:

adjusting means for adjusting the battery energy bolus that will be consumed during each energy consuming incident or the frequency of occurrence of energy consuming incidents per unit of time occurring in the future; and wherein:
the estimating means further comprises means for estimating an estimated future current drain for each channel as a function of the estimated past current drain and the adjusted battery energy bolus; and the determining means further comprises means for scaling the maximum percentile remaining life estimate based upon estimated past current drain to the ratio of the estimated past current drain and the estimated future current drain to derive a scaled maximum percentile remaining life estimate until the battery elective replacement interval voltage is reached.

17. The IMD of claim 13, wherein the estimating means further comprises means for determining, from the estimated past current drain and the average measured battery voltage, a 95th percentile remaining life estimate of the time remaining during which 95% of batteries exhibiting the characteristic voltage drop of the battery voltage when subjected to the estimated past current drain of this type will fall to the elective replacement interval voltage.

18. The IMD of claim 17, and further comprising:

adjusting means for adjusting the battery energy bolus that will be consumed during each energy consuming incident or the frequency of occurrence of energy consuming incidents per unit of time occurring in the future; and wherein:

the estimating means further comprises means for estimating an estimated future current drain for each channel as a function of the estimated past current drain and the adjusted battery energy bolus; and the determining means further comprises means for scaling the 95th percentile remaining life estimate based upon estimated past current drain to the ratio of the estimated past current drain and the estimated future current drain to derive a scaled 95th percentile remaining life estimate until the battery elective replacement interval voltage is reached.

19. The IMD of claim 13, wherein the estimating means further comprises means for determining, from the estimated past current drain and the average measured battery voltage, a minimum percentile remaining life estimate of the time remaining during which a minimum percentage of batteries exhibiting the characteristic voltage drop of the battery voltage when subjected to the estimated past current drain of this type will fall to the elective replacement interval voltage.

20. The IMD of claim 19, and further comprising:

means for adjusting the battery energy bolus that will be consumed during each energy consuming incident or the frequency of occurrence of energy consuming incidents per unit of time occurring in the future; and wherein:

the estimating means further comprises means for estimating an estimated future current drain for each channel as a function of the estimated past current drain and the adjusted battery energy bolus; and the determining means further comprises means for scaling the minimum percentile remaining life estimate based upon estimated past current drain to the ratio of the estimated past current drain and the estimated future current drain to derive a scaled minimum percentile remaining life estimate until the battery elective replacement interval voltage is reached.

21. The IMD of claim 13, wherein the estimating means further comprises means for determining, from the estimated past current drain and the average measured battery voltage, a 5th percentile remaining life estimate of the time remaining during which 5% of batteries exhibiting the characteristic voltage drop of the battery voltage when subjected to the estimated past current drain of this type will fall to the elective replacement interval voltage.

22. The IMD of claim 21, further comprising:

adjusting means for adjusting the battery energy bolus that will be consumed during each energy consuming incident or the frequency of occurrence of energy consuming incidents per unit of time occurring in the future; and wherein:

the estimating means further comprises means for estimating an estimated future current drain for each channel as a function of the estimated past current drain and the adjusted battery energy bolus; and the determining means further comprises means for scaling the 5th percentile remaining life estimate based upon estimated past current drain to the ratio of the estimated past current drain and the estimated future current drain to derive a scaled 5th percentile remaining life estimate until the battery elective replacement interval voltage is reached.

23. The IMD of claim 13, wherein:

the IMD comprises a cardiac pacing system that delivers pacing pulses in energy consuming incidents through a pacing lead and electrode and body tissue comprising a load having an impedance, whereby delivery of each pacing pulse consumes a predetermined bolus of energy, and the estimating means further comprises means for measuring the impedance of the load.

24. The IMD of claim 13, wherein:

the IMD comprises an electrical stimulator that delivers stimulation pulses in energy consuming incidents through an electrode and body tissue comprising a load having an impedance, whereby delivery of each stimulation pulse consumes a predetermined bolus of energy, and the estimating means further comprises means for measuring the impedance of the load.

25. A method of estimating remaining life of a battery that powers an implantable medical device (IMD), comprising the step of:

obtaining a measurement indicative of voltage provided by the battery;

obtaining an estimation of past current drain on the battery; and determining the estimated remaining life of the battery from the measurement indicative of voltage and the estimation of east current drain, wherein obtaining a measurement includes obtaining an average of multiple measurements each indicative of battery voltage.

26. A method of estimating remaining life of a battery that powers an implantable medical device (IMD), comprising the steps of:

obtaining a measurement indicative of voltage provided by the battery;

obtaining an estimation of past current drain on the battery;

determining the estimated remaining life of the battery from the measurement indicative of voltage and the estimation of past current drain, wherein obtaining a measurement includes obtaining a quiescent current drain;

obtaining an episodic current drain; and adding the quiescent current drain and the episodic current drain.

27. A method of estimating remaining life of a battery that powers an implantable medical device (IMD), comprising the steps of:

obtaining a measurement indicative of voltage provided by the battery;

obtaining an estimation of past current drain on the battery;

determining the estimated remaining life of the battery from the measurement indicative of voltage and the estimation of past current drain;

adjusting an operating parameter of the IMD to modify IMD power consumption;

estimating a future current drain at the modified IMD power consumption; and scaling the estimated remaining life of the battery based on the future current drain.

28. A method of estimating remaining life of a battery that powers an implantable medical device (IMD), comprising the steps of:

obtaining a measurement indicative of voltage provided by the battery;

obtaining an estimation of past current drain on the battery; and determining the estimated remaining life of the battery from the measurement indicative of voltage and the estimation of past current drain, wherein determining the estimated remaining life includes determining an estimated remaining life for a predetermined maximum percentage of batteries.

29. A method of estimating remaining life of a battery that powers an implantable medical device (IMD), comprising the steps of:

obtaining a measurement indicative of voltage provided by the battery;

obtaining an estimation of past current drain on the battery; and determining the estimated remaining life of the battery from the measurement indicative of voltage and the estimation of past current drain, wherein determining the estimated remaining life includes determining an estimated remaining life for a predetermined minimum percentage of batteries.

30. A system for monitoring life of a battery, comprising:

a sensing circuit to measure voltage provided by the battery; and a processing circuit coupled to the sensing circuit to calculate past current drain on the battery and to further determine, based on the measured voltage and the past current drain, an estimated remaining life of the battery, wherein the processing circuit includes means for utilizing a quiescent current drain and an episodic current drain to calculate the past current drain.

31. The system of claim 30, and further comprising:

a circuit to adjust an operating parameter of a system coupled to the battery to modify power consumption from the battery; and wherein the processing circuit includes means for estimating a future current drain at a modified power consumption level, and for scaling the estimated remaining life of the battery based on the future current drain.

* * * * *

UNITED STATES PATENT AND TRADEMARK OFFICE
CERTIFICATE OF CORRECTION

PATENT NO. : 6,671,552 B2
APPLICATION NO. : 09/970374
DATED : December 30, 2003
INVENTOR(S) : Donald R. Merritt et al.

It is certified that error appears in the above-identified patent and that said Letters Patent is hereby corrected as shown below:

Colum 16, line 65, please delete "energy bobs;" and insert --energy bolus;--

Column 20, line 46, please delete "of east" and insert --of past--

Signed and Sealed this

Nineteenth Day of December, 2006

JON W. DUDAS
*Director of the United States Patent and Trademark Office*